US012611525B2

(12) United States Patent
Vrancken Peeters et al.

(10) Patent No.: US 12,611,525 B2
(45) Date of Patent: Apr. 28, 2026

(54) GUIDE WIRE-CATHETER ASSEMBLY

(71) Applicant: Mencius Medical B.V., S Gravenhage (NL)

(72) Inventors: Mark-Paul Franciscus Maria Vrancken Peeters, S Gravenhage (NL); Sander Martijn Havik, S Gravenhage (NL)

(73) Assignee: Mencius Medical B.V., 's Gravenhagem (NL)

( * ) Notice: Subject to any disclaimer, the term of this patent is extended or adjusted under 35 U.S.C. 154(b) by 363 days.

(21) Appl. No.: 16/492,792

(22) PCT Filed: Mar. 20, 2018

(86) PCT No.: PCT/NL2018/050175
§ 371 (c)(1),
(2) Date: Sep. 10, 2019

(87) PCT Pub. No.: WO2018/174712
PCT Pub. Date: Sep. 27, 2018

(65) Prior Publication Data

US 2020/0054864 A1 Feb. 20, 2020

(30) Foreign Application Priority Data

Mar. 20, 2017 (NL) ...................................... 2018553
Oct. 4, 2017 (NL) ...................................... 2019670

(51) Int. Cl.
*A61M 25/09* (2006.01)
*A61B 5/00* (2006.01)
(Continued)

(52) U.S. Cl.
CPC ... *A61M 25/09041* (2013.01); *A61B 5/14539* (2013.01); *A61B 5/6852* (2013.01);
(Continued)

(58) Field of Classification Search
CPC .. A61M 2025/0063; A61M 2025/0161; A61M 25/09025; A61M 25/0147
See application file for complete search history.

(56) References Cited

U.S. PATENT DOCUMENTS 5,674,197 A * 10/1997 van Muiden ..... A61M 25/0141
604/524
2002/0082610 A1* 6/2002 Cioanta ................... A61B 18/04
623/1.11
(Continued)

FOREIGN PATENT DOCUMENTS

EP 0 689 851 A1 1/1996
EP 1 800 708 A1 6/2007
(Continued)

*Primary Examiner* — William R Carpenter
(74) *Attorney, Agent, or Firm* — Hoffmann & Baron, LLP

(57) ABSTRACT

A guide wire-catheter assembly includes a catheter tube having a longitudinal channel, and a guide wire configured to be movable in the longitudinal channel. The catheter tube includes a bendable part near its distal end. The bendable part includes, in the circumferential direction of the catheter tube, a varying flexibility, such that exerting a longitudinal compression force in a proximal direction at a compression location distally of the distal end part results in bending of the bendable part. The guide wire includes an expandable part, where the expandable part is movable between a non-expanded position, in which a cross section of the expandable part is smaller than a smallest cross section of the longitudinal channel of the catheter tube and an expanded position. When the expandable part is in the non-expanded position, the guide wire can be moved completely in and out of the longitudinal channel of the catheter tube.

24 Claims, 8 Drawing Sheets

(51) Int. Cl.

| | |
|---|---|
| *A61B 5/145* | (2006.01) |
| *A61J 15/00* | (2006.01) |
| *A61M 25/00* | (2006.01) |
| *A61M 25/01* | (2006.01) |

(52) U.S. Cl.

CPC ...... *A61J 15/0007* (2013.01); *A61M 25/0054* (2013.01); *A61M 25/0108* (2013.01); *A61M 2025/0004* (2013.01); *A61M 2025/09075* (2013.01); *A61M 2025/09125* (2013.01); *A61M 2025/09166* (2013.01); *A61M 2205/3327* (2013.01)

(56) References Cited

U.S. PATENT DOCUMENTS

| | | | | |
|---|---|---|---|---|
| 2003/0199960 | A1* | 10/2003 | Paskar | A61M 25/0041 607/122 |

| | | | | |
|---|---|---|---|---|
| 2005/0113862 | A1 | 5/2005 | Besselink et al. | |
| 2005/0131343 | A1* | 6/2005 | Abrams | A61M 25/0662 606/41 |
| 2007/0149898 | A1* | 6/2007 | Inderbitzen | A61M 25/0141 600/585 |
| 2011/0196410 | A1 | 8/2011 | Besselink et al. | |
| 2012/0184955 | A1* | 7/2012 | Pivotto | A61B 34/30 606/41 |
| 2013/0237755 | A1* | 9/2013 | Singh | A61B 1/012 600/109 |
| 2015/0099936 | A1* | 4/2015 | Burdulis | A61N 1/36071 604/523 |

FOREIGN PATENT DOCUMENTS

| | | |
|---|---|---|
| EP | 2 893 951 A1 | 7/2015 |
| WO | 2006/119503 A1 | 11/2006 |
| WO | 2012/178073 A1 | 12/2012 |

* cited by examiner

Figure 11
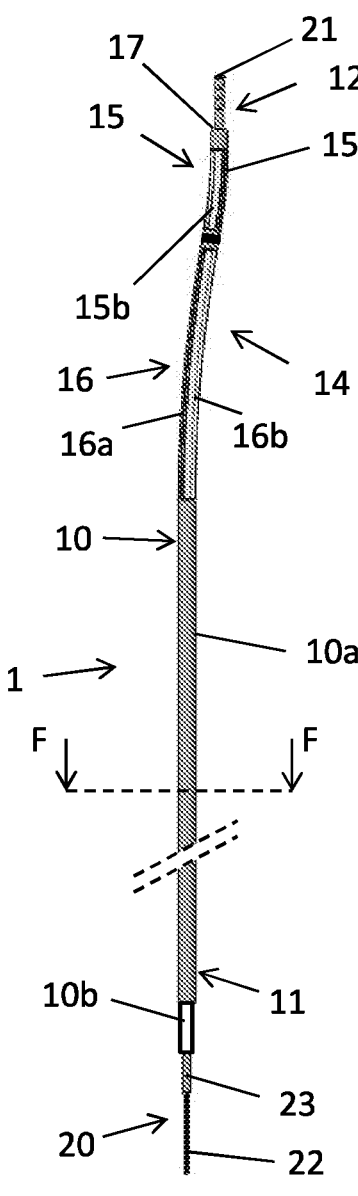
Figure 12 (F-F)
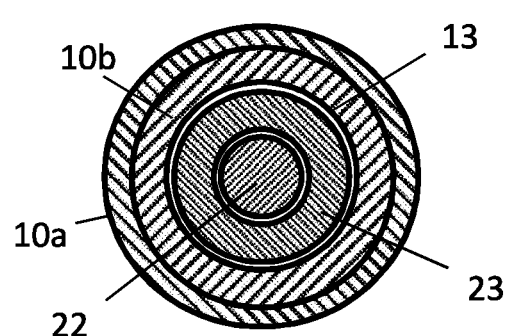

Figure 17

GUIDE WIRE-CATHETER ASSEMBLY

CROSS-REFERENCE TO RELATED APPLICATIONS

This application is the National Stage of International Application No. PCT/NL2018/050175, filed Mar. 20, 2018, which claims the benefit of Netherlands Application Nos. 2018553, filed Mar. 20, 2017, and U.S. Pat. No. 2,019,670, filed Oct. 4, 2017, the contents of all of which are incorporated by reference herein.

FIELD OF THE INVENTION

The present invention relates to a guide wire-catheter assembly for use in a body lumen, in particular the vascular system. There is a need to have a steerable catheter that can easily and reliably be navigated through the vascular tree of a human or animal body.

BACKGROUND OF THE INVENTION

Conventional guide wire-catheter assemblies comprise a catheter tube having a longitudinal channel and a guide wire, configured to be movably arranged in the longitudinal channel of the catheter tube.

The guide wire is used to maneuver and guide the catheter tube through the vascular system of the human or animal body to locate the catheter at a desired location, for instance in a coronary artery. This guiding of the catheter tube requires relative movement of the guide wire and possibly exchange of guide wires (and/or catheter tubes) having different shapes, in order to maneuver the guide wire and subsequently the catheter through tortuous passageways in the vascular system.

A drawback of the conventional guide wire-catheter assemblies is that advancing the guide wire through the catheter tube channel, to accomplish advancing the guide wire-catheter assembly through a vessel, always results in a dynamic shape change of the distal end of the guide wire-catheter assembly, which makes precise maneuvering of the distal end of the guide wire-catheter assembly difficult.

SUMMARY OF THE INVENTION

An aim of the present invention is to provide a guide wire-catheter assembly having improved maneuverability, while at the same time having a diameter comparable with conventional prior art guide wire-catheter assemblies. For example, a 2 mm (6 Fr) or less outer diameter catheter, for example, is normally used in peripheral arterial interventions.

The invention provides a guide wire-catheter assembly as described herein.

The guide wire-catheter assembly of the invention comprises a catheter tube having a bendable part near its distal end. This bendable part comprises a varying flexibility in circumferential direction, in order to allow bending of the bendable part by exerting a longitudinal compression force at a compression location distally of the bendable part.

The longitudinal compression force is a force that is exerted, at a compression location, in longitudinal direction on the circumference of the catheter tube in order to bend the distal part of the catheter tube.

The guide wire is used to exert this longitudinal compression force at the compression location, so that no separate part is needed to control bending of the bendable part. However, in order to use the guide wire properly, the guide wire has to be exchangeable in the longitudinal channel of the catheter, even when the catheter remains partly in the human or animal body. Thus, the guide wire has to be completely movable in and out of the longitudinal channel of the catheter tube, and at the same time be capable of exerting a longitudinal compression force on the catheter tube distally of the bendable part.

Therefore, the guide wire comprises an expandable part movable between a non-expanded position and an expanded position. In the non-expanded position, the cross section of the expandable part is smaller than the smallest cross section of the longitudinal channel, such that the guide wire can be moved completely in and out of the longitudinal channel, to allow exchange of the guide wire (or any other feed wire) in the catheter.

In the expanded position of the expandable part, a cross section of the expandable part is larger than the smallest cross section of the longitudinal channel, such that the exertion of a longitudinal compression force on the bendable part, by pulling the feed wire in proximal direction, results in bending of the bendable part.

The main advantage of the guide wire-catheter assembly of the invention, is that the shape of the guide wire-catheter assembly, in particular the shape of the distal end of the guide wire-catheter assembly, can be adjusted to a certain desired curved shape, and can be maintained in this curved shape by maintaining the relative position of the guide wire with respect to the catheter tube. This possibility to hold the distal end of the guide wire-catheter assembly in a desired static curved shape, even when advancing the guide wire-catheter assembly in the respective blood vessel, allows for an improved maneuvering of the guide wire-catheter assembly through the vessel, in particular in tortuous passageways.

Thereby, the guide wire-catheter assembly is a relatively simple construction, allowing the guide wire-catheter assembly to have a relatively small diameter similar to conventional guide wire-catheter assemblies, For example 2 mm (6 Fr) or less outer diameter catheters for peripheral arterial interventions). Only two parts may be required, i.e. a guide wire and a catheter tube, to obtain the improved maneuverability of the guide wire-catheter assembly of the invention.

In an embodiment, the expandable part is arranged at a distal end of the guide wire. The expandable part of the guide wire may be arranged at any suitable location, but is preferably arranged at or close to the distal end of the guide wire. In such embodiment, the guide wire will not extend (too far) distally from the catheter tube when the expandable part is held at the compression location in the catheter tube channel. For example, the expandable part of the guide wire is arranged proximally adjacent to a flexible tip of the guide wire.

The guide wire may also comprise multiple expandable parts arranged at different locations along the guide wire. Dependent on the relative position of the guide wire, in particular the expandable part, with respect to the catheter tube, one or more of the different expandable parts may cooperate with one or more compression locations arranged along the distal end of the catheter tube.

In an embodiment, the guide wire comprises a longitudinal guide wire sleeve and a core wire, wherein the expandable part is movable between the non-expanded position and the expanded position by longitudinal movement between the guide wire sleeve and the core wire. In an alternative embodiment, the expandable part comprises an inflatable element, such as a balloon, provided at or near the distal end of the guide wire. The guide wire may comprise an inflation lumen running from the inflatable element to a proximal end of the guide wire. A fluid, for example provided by a fluid pump, may be used to move the inflatable element between a deflated state, corresponding to the non-expanded position, and an inflated state, corresponding to the expanded position. Any other suitable expandable part may also be applied.

In order to allow the movement of the expandable part of the guide wire between the non-expanded position and the expanded position, when at least the distal end of the guide wire-catheter assembly is placed in a human or animal body, manipulation at the proximal end of the guide wire, or manipulation somewhere in between the proximal end and the distal end of the guide wire, should result in the movement between the non-expanded position and the expanded position. Relative longitudinal movement of the guide wire sleeve with respect to a core wire enables such proximal manipulation to enable movement of the expandable part between the non-expanded position and the expanded position with a relatively simple construction.

The expandable part may for example comprise a bellows shaped sleeve part, wherein one end of the bellows is connected to the core wire and the other end of the bellows is connected to the guide wire sleeve. By movement of the one end of the bellows towards the other end of the bellows, the bellows can be brought in the expanded position, while movement of the one end of the bellows and the other end of the bellows away from each other, the bellows can be brought in the non-expanded position.

In an embodiment, the compression location of the catheter tube is formed by a distal end surface of the catheter tube, defining a distal opening of the longitudinal channel. In this embodiment, the expandable part can be arranged in the expanded position, when the expandable part extends distally from the catheter tube, and can be drawn in proximal direction back into the catheter tube, until the expandable part reaches the distal end surface, where further movement of the guide wire in the proximal direction is prevented and a longitudinal compression force can be exerted on the catheter tube. This configuration, comprising the distal end surface as a compression location for the expandable part, allows a relative easy and reliable positioning of the expandable part with respect to the compression location.

In an embodiment, the bendable part comprises multiple compression locations arranged at different longitudinal positions of the longitudinal channel of the catheter tube. The multiple compression locations may be formed by a friction-fit connection on the inner surface of the catheter tube, i.e. the expandable part is expanded at a desired compression location to connect the expandable part with the catheter tube by exerting a force on the inner surface of the longitudinal channel of the catheter tube.

The multiple compression locations are preferably formed by ribs, rims, grooves or other gripping elements arranged on the inner surface of the catheter may be provided to couple the expandable tip part to the catheter tube 10. These form-fit connections have the advantage that they can provide a very reliable mechanical coupling between the expandable part and the catheter tube. Furthermore, the gripping elements also define the location of the expandable part with respect to the catheter tube. This enables the user to place the expandable part at the desired compression location. This can for example be done by sliding the expandable part, when partly expanded, in proximal direction until the expandable part will be stopped by the gripping elements, indicating that the desired compression location is reached.

In an embodiment, the bendable part comprises a first material, extending over a first part of a circumference of the catheter tube, and a second material, extending over a second part of the circumference of the catheter tube, wherein the first material has a first stiffness and the second material has a second stiffness, wherein the first stiffness is larger than the second stiffness such that exerting the longitudinal compression force on the bendable part, by pulling the guide wire in proximal direction, causes bending of the bendable part.

By providing in the circumferential direction of the bendable part of the catheter tube a first material and a second material, wherein the first material and the second material have a different stiffness, bending of the bendable part can be facilitated, whereby the bending direction and degree of bending can be reliably predicted and controlled by the longitudinal compression force exerted on the bendable part by pulling of the guide wire in proximal direction.

Further, the first material and the second material can be shaped to form a cylindrical body having a smooth outer surface without the need of a separate covering sleeve.

In this embodiment, the bendable part of the catheter tube may have a constant thickness in the circumferential direction, while, at the same time, the catheter tube and guide wire are arranged concentrically with respect to each other. This provides a compact construction and a predictable bending direction of the catheter tube when a compression force is exerted on the bendable part. This bending direction is independent of the rotational position of the guide wire.

In alternative embodiments, grooves, recesses or openings may be provided to decrease the stiffness on one side of the catheter tube, and/or reinforcements may be provided to increase the stiffness on another side of the catheter tube, in order to facilitate bending of the bendable part.

In an embodiment, the bendable part comprises a first bendable sub-part and a second bendable sub-part, wherein the first bendable sub-part is configured to bend in a first bending direction, and wherein the second bendable sub-part is configured to bend in a second bending direction, wherein the first bending direction and the second bending direction are preferably different. By provision of two bendable sub-parts, the first bendable sub-part may be provided for bending of the catheter tube in a first bending direction, and the second bendable sub-part may be provided for bending of the catheter tube in a second bending direction.

A compression location of the catheter tube may be arranged distally of both the first bendable part and the second bendable part, such that exerting a longitudinal compression force in a proximal direction at the compression location, for example created by pulling the guide wire in proximal direction, results in bending of both the first bendable part and the second bendable part. Also, a second compression location may be arranged between the first bendable part and the second bendable part, such that exerting a longitudinal compression force in a proximal direction at the second compression location results in bending of only the bendable sub-part arranged proximally of the second compression location.

The second compression location is preferably formed by ribs, rims, grooves or other gripping elements arranged on the inner surface of the catheter may be provided to couple the expandable part to the catheter tube.

In an embodiment, the first bendable sub-part and the second bendable sub-part each comprises a first material extending over a first part of a circumference of the catheter tube, and a second material extending over a second part of the circumference of the catheter tube, wherein the first material has a first stiffness and the second material has a second stiffness, wherein the first stiffness is larger than the second stiffness, such that exerting a longitudinal compression force on the catheter tube causes bending of the first bendable sub-part and the second bendable sub-part.

When a first material and a second material in the circumferential direction of the catheter tube are used to provide bendability to the catheter tube in a certain desirable bending direction, the first and second material in the first bendable sub-part may be different than the first and second material in the second bendable sub-part, in order to obtain a different bending behavior of the first bendable sub-part compared to the second bendable sub-part. The difference is the first and second material may for example be a different stiffness of the first and/or second material, a different circumferential distribution of the first and second material, a different thickness of the first and/or second material, etc. The resulting bending behavior may for example be different in a degree of bending and/or a different bending direction.

In an embodiment, the bendable part comprises a first bendable sub-part and a second bendable sub-part, wherein the first bendable sub-part is configured to bend in a first bending direction, and wherein the second bendable sub-part is configured to bend in a second bending direction, and wherein the second bendable sub-part is rotatable about a longitudinal axis of the catheter tube with respect to the first bendable sub-part, to adjust the first bending direction with respect to the second bending direction.

By enabling rotation of the first bendable sub-part with respect to the second bendable sub-part, the first bending direction of the first bendable sub-part can be adjusted with respect to the second bending direction of the second bendable sub-part. This provides more possibilities to adapt the shape of the catheter tube to the desired shape of the vessel passageway, in which the guide wire-catheter assembly should be advanced.

In an embodiment, the first bendable sub-part and the second bendable sub-part are connected to each other by a rotation coupling, that allows rotation of the first bendable sub-part and the second bendable sub-part with respect to each other. The rotation coupling may for example be formed by a circumferential groove provided in the first bendable sub-part that cooperates with a circumferential rim provided on the second bendable sub-part.

Such rotation coupling may allow easy rotation of the first bendable sub-part with respect to the second bendable sub-part, while the first bendable sub-part cannot be disconnected from the second bendable sub-part, or only be disconnected by exerting an excessive pulling force. To adjust the rotational position of the first bendable sub-part with respect to the second bendable sub-part, the catheter tube may be moved outside the human or animal body. However, it may, in some embodiments also be possible to adjust the rotational position of the first bendable sub-part with respect to the second bendable sub-part by rotation of the guide wire, while the expandable part of the guide wire engages the most distal of the first and second bendable sub-parts. This engagement may for example be created by expanding the expandable part at a rotation location where the expandable part can engage the distal bendable sub-part with sufficient force to transfer a rotation of the guide wire to a rotation of the distal bendable sub-part.

To prevent that the rotational position of the first bendable sub-part with respect to the second bendable sub-part undesirably changes when advancing the guide wire-catheter assembly in a human or animal body some friction between the groove and the rim may be provided.

In an alternative embodiment, the first bendable sub-part is arranged distally from the second bendable sub-part, wherein the catheter tube comprises a catheter outer tube and a catheter inner tube, wherein the catheter inner tube is at least partially arranged in the catheter outer tube and wherein the first bendable sub-part is connected to the catheter inner tube, and wherein the second bendable sub-part is connected to the catheter outer tube.

By providing a catheter inner tube and a catheter outer tube, that extend both to a proximal end of the guide wire-catheter assembly, the rotational position of the first bendable sub-part with respect to the second bendable sub-part may be adapted by rotation of the catheter inner tube and the outer catheter tube with respect to each other. Since the catheter inner tube and the catheter outer tube extend to the proximal end of the guide wire-catheter assembly, that is not introduced into the human or animal body, the rotational position of the first bendable sub-part with respect to the rotational position of the second bendable sub-part may be adjusted without the need of pulling the catheter tube out of the human or animal body.

In an embodiment, the guide wire-catheter assembly comprises a locking device to lock a position of the guide wire with respect to the catheter tube. As explained above, holding the guide wire in a fixed position with respect to the catheter tube, while the expandable part exerts a longitudinal compression force on the compression location, ensures that the bendable part remains in a constant bent shape, even when the guide wire-catheter assembly is further advanced into the vessel. This constant bent shape enables relatively easy maneuvering of the distal end of the guide wire-catheter assembly in the vessel. By providing a locking device, the position of the guide wire with respect to the catheter tube may be locked, so that the desired bent shape is maintained without the need of the guide wire and the catheter tube to be continuously held by the surgeon manipulating the guide wire-catheter assembly.

The guide wire-catheter assembly of the invention provides an easy to use and easy to maneuver guide wire-catheter assembly, while having at the same time an equal or even smaller diameter than conventional guide wire-catheter assemblies. For example, an outer diameter of the catheter-tube may be maximally 3.0 mm, preferably maximally 2.5 mm, more preferably maximally 2.0 mm. An outer diameter of the guide wire with the expandable part in a non-expanded position may be maximally 2.0 mm, preferably maximally 1.0 mm.

In an embodiment, the guide wire-catheter assembly, or one of its individual components, i.e. the catheter-tube or the guide wire, comprises one or more markers of radiopaque material. For example, the markers may be ring shaped elements arranged at the proximal end and/or distal end of the bendable part and/or ring-shaped elements arranged at the proximal end and/or distal end of the expandable part. Any other type of markers that can be detected from outside the human or animal body with x-ray or any other imaging modality/device may also be used to improve visibility of the guide wire-catheter assembly in a human or animal body.

In an embodiment, the guide wire-catheter assembly comprises an operating device to lock the relative position of the guide wire core with respect to the guide wire sleeve in at least a first locking position in which the expandable part is arranged in the non-expanded position and a second locking position in which the expandable part is arranged in the expanded position. During use, it is advantageous that the relative position of the guide wire core with respect to the guide wire sleeve can be locked in relative positions that correspond with the expanded position and the non-expanded position of the expandable part.

The operating device may for example comprise two parts that are axially movable with respect to each other between two locking positions, whereby the guide wire core is fixed to one of the two parts and the guide wire sleeve is fixed to the other of the two parts.

In an embodiment, the guide wire-catheter assembly comprises an operating device to adjust a relative position of a proximal end of the guide wire with respect to a proximal end of the catheter tube. This adjustment of a relative position may be used to adjust the compression force that is exerted by the expandable part in expanded position on the catheter tube at a compression location where the expandable part is in contact with the catheter tube. The adjustment of the relative position of the proximal end of the guide wire with respect to the proximal end of the catheter tube may also be used to move the expandable part with respect to the catheter tube, for example to move the expandable part to a desired compression location.

In an embodiment, the operating device comprises a first operating part and a second operating part, wherein the first operating part comprises a first screw thread and the second operating part comprises a second screw thread mating with the first screw thread, wherein the proximal end of the catheter tube is fixed to the first operating part and the proximal end of the guide wire is connected to the second operating part.

It is remarked that an operating device may be arranged to lock the relative position of the guide wire core with respect to the guide wire sleeve and to adjust a relative position of a proximal end of the guide wire with respect to a proximal end of the catheter tube.

In an embodiment, the catheter tube comprises a sensor arranged to provide a sensor signal representative for a degree of bending of the catheter tube. When a catheter tube is brought into a patient, the introduction path along which the catheter tube bends should be known to a large extent. When the bending of the catheter tube substantially deviates from the bending that could be expected on the basis of the position of the catheter tube and its intended introduction path, this is a strong indication that the catheter tube does not extend along the desired introduction path. In such situation, the catheter tube may be at least partially retracted and reintroduced to guide the catheter tube along the intended insertion path.

The sensor may for example be a piezo-electric, a wire strain gauge or an optical sensor such as a Fiber Bragg grating, or any other sensor device capable of measuring a signal representative for the bending of the catheter tube.

Multiple sensors arranged to provide a sensor signal representative for a degree of bending of the catheter tube may be arranged along the length of the catheter tube to determine the bending of the catheter tube at different locations of the catheter tube.

In an embodiment, the catheter tube is a feeding tube to be placed through a mouth or a nose of a patient into the stomach or small intestine of the patient. Such feeding tube may for instance be nasogastric feeding tube to be placed with its feeding end into the stomach, a nasojejunal feeding tube to be placed with its feeding end into a middle section of the small intestine and a nasoduodenal feeding tube to be placed with its feeding end into a first section of the small intestine. Similar feeding tubes, such as an orogastric feeding tube, an orojejunal feeding tube, and an oroduodenal feeding tube may be introduced via the mouth into the patient.

Often it may be challenging to introduce such feeding tube along the desired introduction path through the esophagus into the stomach and small intestine. The catheter tube of the invention allows the user to adapt the shape of the distal end of the catheter tube by bending of the bendable part in order to facilitate the introduction of the catheter tube into the patient. the catheter tube of the present invention may obviate the need to use an endoscope for the introduction of a feeding tube into the body of a patient. Also, monitoring the position of the tube is sometimes necessary. An endoscope uses camera imaging for this, but visual feedback is often obstructed inside the intestines. Also radiology is sometimes used to monitor the position of the tube. Radiologic solutions require additional equipment and may also be harmful to the patient. A bending sensor can provide an alternative way to monitor the tube's position.

In an embodiment, the catheter tube comprises a pH sensor configured to provide a pH sensor signal representative for a pH value at a location of the pH sensor. Such pH sensor may for example be provided at or near the distal end of the catheter tube.

When the catheter tube is a feeding tube, the pH value as determined by the pH sensor can be used to determine whether the catheter tube, at the position of the pH sensor, has moved from the stomach to the small intestine. This information can be used to confirm the correct positioning of the catheter tube along the desired insertion path.

BRIEF DESCRIPTION OF THE DRAWINGS

An embodiment of a guide wire-catheter assembly according to the invention will now be described in further detail, by way of example only, with reference to the accompanying drawings, in which:

FIG. 2 shows a cross section A-A of the guide wire-catheter assembly of FIG. 1;

FIG. 3 shows a cross section B-B of the guide wire-catheter assembly of FIG. 1;

FIG. 4 shows a cross section C-C of the guide wire-catheter assembly of FIG. 1;

FIG. 9 shows a cross section D-D of the guide wire-catheter assembly of FIG. 8;

FIG. 10 shows a cross section E-E of the guide wire-catheter assembly of FIG. 8;

FIG. 11 shows a guide wire-catheter assembly according to a further alternative embodiment of the invention;

FIG. 12 shows a cross section F-F of the guide wire-catheter assembly of FIG. 11

FIG. 17 shows a guide wire-catheter assembly according to another embodiment of the invention.

DETAILED DESCRIPTION OF THE INVENTION

Figure 1:
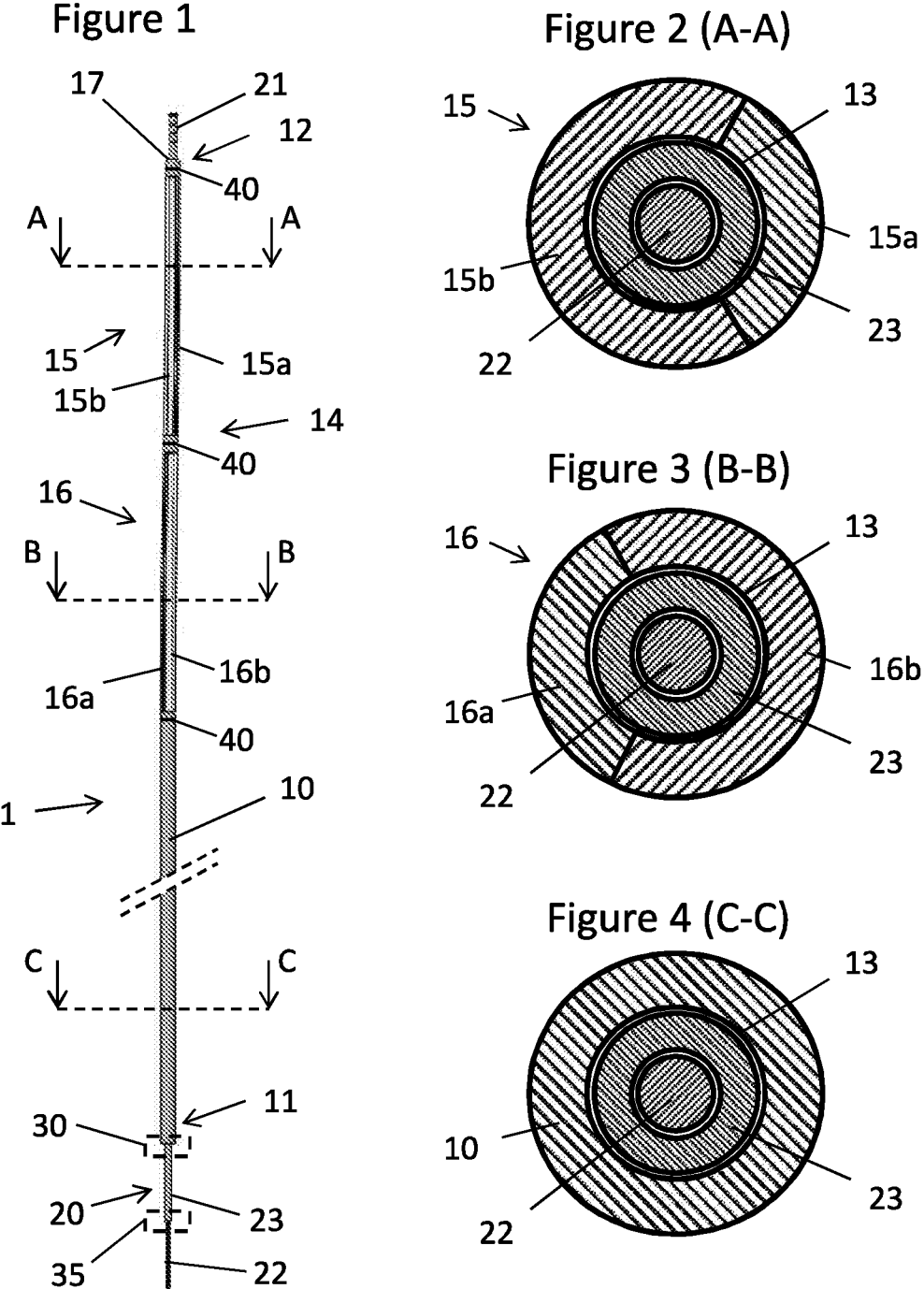
FIG. 1 shows a guide wire-catheter assembly according to an embodiment of the invention.

FIG. 1 shows a guide wire-catheter assembly, generally indicated by reference numeral 1. FIGS. 2, 3, and 4 show cross sections A-A, B-B and C-C at different locations of the guide wire-catheter assembly 1. The guide wire-catheter assembly 1 comprises a catheter tube 10 and a guide wire 20. The catheter tube 10 and the guide wire 20 are elongate elements configured to be arranged in, and advanced through, a body lumen, in particular a lumen of the vascular system.

FIG. 1 shows only a distal end part and a proximal end part of the catheter assembly 1.

The catheter tube 10 comprises a proximal end 11 and a distal end 12. A longitudinal channel 13 runs from the proximal end 11 to the distal end 12 of the catheter tube 10.

The guide wire 20 is dimensioned to be freely movable in the longitudinal channel in the longitudinal direction of the longitudinal channel 13. The guide wire 20 may be completely moved out of the longitudinal channel 13 and for example be replaced by another guide wire. Correspondingly, the catheter tube 10 may be completely slid over the guide wire 20 in the proximal direction in order to exchange the catheter tube 10, while the guide wire 20 remains in a body lumen.

The catheter tube 10 comprises near its distal end 12 a bendable part 14. The bendable part 14 comprises a distal bendable sub-part 15 and a proximal bendable sub-part 16.

As also can be seen in FIG. 2, the distal bendable sub-part 15 comprises a first material part 15*a* extending over a first part of a circumference of the catheter tube 10, and a second material part 15*b* extending over a second part of the circumference of the catheter tube 10. The material of the first material part 15*a* has a first stiffness and the material of the second material part 15*b* has a second stiffness. The first stiffness is larger than the second stiffness.

Similarly, as can be seen in FIG. 3, the proximal bendable sub-part 16 comprises a first material part 16*a* extending over a first part of a circumference of the catheter tube 10, and a second material part 16*b* extending over a second part of the circumference of the catheter tube 10. The material of the first material part 16*a* has a first stiffness and the material of the second material part 16*b* has a second stiffness, wherein the first stiffness is larger than the second stiffness.

Due to the difference in stiffness between the first material part 15*a* and the second material part 15*b*, the distal bendable sub-part 15 will bend when a longitudinal compression force is exerted on a compression location formed by a distal end surface 17 of the catheter tube 10. Correspondingly, due to the difference in stiffness between the first material part 16*a* and the second material part 16*b*, the proximal bendable sub-part 16 will also bend when a longitudinal compression force is exerted on a distal end surface 17 of the catheter tube 10.

The relatively stiff first material part 15*a* of the distal bendable sub-part 15 is arranged, at an opposite side of the cross section, compared to the relatively stiff first material part 16*a* of the proximal bendable sub-part 16. As a result, the distal bendable sub-part 15 will bend, when a longitudinal compression force is exerted on the distal end surface 17 in a different bending direction compared to the proximal bendable sub-part 16. In particular, the bendable part 15 and bendable part 16 will have an S-shape when a longitudinal compression force is exerted on the distal end surface 17.

It is remarked that, as can be seen in FIGS. 2 and 3, the catheter tube 10 has at least in its circumferential direction a constant thickness. Furthermore, the catheter tube 10 and the guide wire 20 are arranged concentrically. This provides a relatively compact construction. Furthermore, the varying flexibility of the catheter tube 10 in circumferential direction provides a predictable bending direction of the catheter tube 10 independent of the rotational position of the guide wire 20 in the catheter tube 10.

In order to exert a longitudinal compression force on the distal end surface 17 of the catheter tube 10, the guide wire 20 comprises an expandable tip part 21. The expandable tip part 21 is movable between a non-expanded position, as shown in FIG. 5*a*, and an expanded position, as shown in FIG. 5*b*.

The guide wire 20 comprises a guide wire core 22 and a guide wire sleeve 23. The guide wire sleeve 23 comprises a longitudinal lumen through which the guide wire core 22 extends over the length of the guide wire sleeve 23. At the distal end, the guide wire sleeve 23 is connected to a proximal end of a bellows shaped sleeve part 24 which forms the expandable part 21. The distal end of the bellows shaped sleeve part 24 is connected to a distal end 25 of the guide wire core 22.

Figures 5A, 5B, 6, 6A:
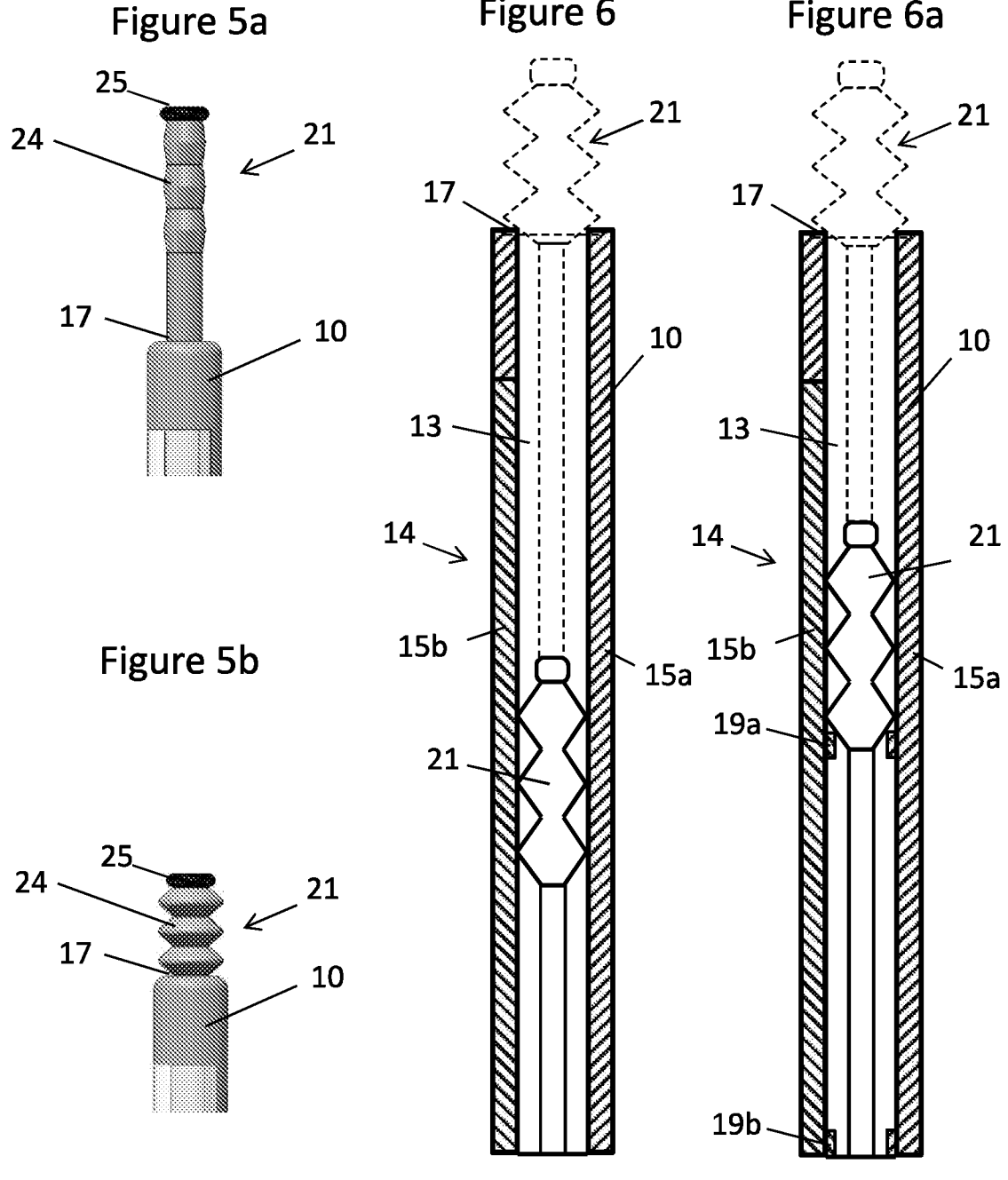
FIG. 5a shows a distal end of the guide wire-catheter assembly of FIG. 1 with an expandable tip in non-expanded position.
FIG. 5b shows a distal end of the guide wire-catheter assembly of FIG. 1 with the expandable tip in expanded position.
FIG. 6 shows a cross section of the distal end part of the guide wire-catheter assembly of FIG. 1.
FIG. 6a shows an alternative embodiment of a cross section of the distal end part of the guide wire-catheter assembly of FIG. 1.

When the expandable tip part 21 protrudes from the distal end of the channel as shown in FIGS. 5 and 6, the guide wire 20 also extends from the proximal end 11 of the catheter tube 10. Further, the proximal end of the guide wire core 22 protrudes from the longitudinal lumen of the guide wire sleeve 23, so that both the proximal end of the guide wire core 22 and the guide wire sleeve 23 can be manipulated by the user. By longitudinal movement of the guide wire core 22 with respect to the guide wire sleeve 23, the expandable tip part 21 can be moved between the non-expanded position and the expanded position by extension and compression of the bellows shaped sleeve part 24.

A guide wire locking device 35 may be provided to lock a relative position of the guide wire core 22 with respect to the guide wire sleeve 23. By locking the relative position of the guide wire core 22 with respect to the guide wire sleeve 23, the expandable tip part 21 can be locked in the expanded position or non-expanded position without the need that the surgeon continuously holds the guide wire core 22 in a fixed position with respect to the guide wire sleeve 23.

In the shown embodiment, the guide wire locking device 35 is provided at the location where the guide wire core 22 protrudes proximally from the guide wire sleeve 23. In an alternative embodiment, the guide wire locking device 35 may be configured to lock the relative position of the guide wire core 22 with respect to the guide wire sleeve 23 at another location, for example by placing a locking pin through the guide wire sleeve 23 to hold the guide wire core 22, or by clamping the guide wire sleeve 23 with a clamp device such that the guide wire core 22 cannot be displaced with respect to the guide wire sleeve 23. Such alternative embodiment of the guide wire locking device 35 may be advantageous since a length of the guide wire 20 may be substantially larger than a length of the catheter tube 10. Typically, the length of the guide wire 20 may be at least twice the length of the catheter tube, for example for exchange of the catheter tube while the guide wire remains in place in the (vascular) lumen of the human or animal body.

In the non-expanded position, shown in FIG. 5a, a maximum diameter of the expandable tip part 21 is smaller than the minimum diameter of the channel 13 of the catheter tube 10, so that the catheter tube 10 and the guide wire 20 can be moved freely with respect to each other in the longitudinal direction of the guide wire-catheter assembly 1. This also allows the user to exchange, when desired, the catheter tube 10 or the guide wire 20.

In the expanded position, shown in FIG. 5b, the maximum diameter of the expandable tip part 21 is larger than the minimum diameter of the channel 13 of the catheter tube 10, in particular larger than the diameter of the distal opening of the channel 13 provided in the distal end surface 17 of the catheter tube 10. Thus, when the expandable tip part 21 is moved into the expanded position, and subsequently pulled against the distal end surface 17 by exerting a pulling force on the proximal end of the guide wire 20, in particular the guide wire core 22, a longitudinal compression force can be exerted on the bendable part 14 when the catheter tube 10 is held in a fixed position. As described above, such longitudinal compression force will cause bending of the bendable part 14, in particular bending of the distal bendable sub-part 15 in a first bending direction, and bending of the proximal bendable sub-part 16 in a second bending direction.

In dependence of the quantity of the longitudinal compression force, the degree of bending of the bendable part will change. An advantage of the guide wire-catheter assembly 1 is that by maintaining the catheter tube 10 in a fixed relative position with respect to the guide wire 20, the degree of bending of the bendable part 14 can be maintained. Therewith, the bendable part 14 can be held in a constant shape independent of movements made by the guide wire-catheter assembly 1 as a whole. Such static curved shape of the bendable part 14 can be very useful when advancing the guide wire-catheter assembly through a relatively complex luminal structure, such as for example a vascular system of a human.

The guide wire-catheter assembly 1 may comprise a locking device 30 to lock a position of the guide wire 20 with respect to the catheter tube 10, to maintain a static curved shape of the guide wire-catheter assembly without the need of the user continuously holding the catheter tube 10 and the guide wire 20 in a fixed relative position with respect to each other.

A further advantage of the guide wire-catheter assembly 1 is that the bendable part 14 forms a cylindrical body having a smooth outer surface without the need of a separate covering sleeve. The use of material parts 15a, 15b, 16a, 16b having different stiffness instead of different shapes provides a smooth outer surface.

The guide wire-catheter assembly 1 may be made of any suitable material. Generally, the catheter tube 10 may be made of a suitable plastics material, such as polyamide, polyurethane and/or PTFE, and the guide wire 20 may be made of metal, such as stainless steel or nitinol, or other suitable metal materials.

The guide wire-catheter assembly 1 may have cross section dimensions equal or smaller than conventional guide wire-catheter assemblies. Typically, an outer diameter of the catheter tube 10 may be maximally 3.0 mm, preferably maximally 2.5 mm, more preferably maximally 2.0 mm. A maximal outer diameter of the guide wire 20 with the expandable tip part 21 in the non-expanded position may be maximally 1.0 mm, preferably maximally 0.8 mm.

The length of the catheter tube 10 and the guide wire 20 may be dependent on the application for which they are used, and may for example be in the range of 0.5 m-2.0 m, preferably between 0.8 m and 1.5 m. The bendable part 14, and the bendable sub-parts 15, and 16 may have any suitable length. For example, the distal bendable sub-part 15 and the proximal bendable sub-part 16 may each have a length of 5 cm.

It is remarked that, the guide wire-catheter assembly, or one of its individual components, i.e. the catheter tube and/or the guide wire, comprises one or more markers, for example marker rings 40 (FIG. 1) of radiopaque material, or any other suitable detectable material.

FIG. 6 shows a cross section of the distal end part of the guide wire-catheter assembly of FIG. 1. The expandable tip part 21 is shown in dashed lines in a position corresponding to the position shown in FIG. 5b, while the expandable tip part 21 is in the expanded position. As explained above, the expandable part 21 abuts, in this position, against the distal end surface 17. By pulling the guide wire 20 in proximal direction a longitudinal compression force may be exerted on the catheter tube 10 in order to bend the bendable part 14.

In solid lines, the expandable part 21 is drawn at another position with respect to the catheter tube 10, in particular another longitudinal position within the longitudinal channel 13. The expandable tip part 21 is moved to this position while being in the non-expanded position, and subsequently brought into the expanded position to firmly press the expandable tip part 21 against the inner wall of the longitudinal channel 13. Due to this friction-fit arrangement of the expandable tip part 21 in the longitudinal channel 13 at a second compression location, a longitudinal compression force can be exerted on the part of the bendable part 14 proximal from this second compression location. As a result of this different compression location, a compression force exerted on the catheter tube 10 will only result in bending of the part of the bendable part 14 proximal of the second compression location.

It will be clear for the person skilled in the art, that the expandable tip part 21 may also be arranged at other compression locations. It may for example be advantageous to use the transition part between the first bendable sub-part 15 and the second bendable sub-part 16 as a compression location. Exerting a longitudinal compression force at this compression location will only result in bending of the second bendable sub-part 16.

In the shown embodiment of FIG. 6, the connection in the longitudinal channel 13 between the expandable tip part 21 and the catheter tube 10 is created by a friction-fit.

In an alternative embodiment, ribs, rims or other gripping elements may be provided to improve the grip between the expandable tip part 21 and the catheter tube 10. FIG. 6a shows such alternative embodiment of a guide wire-catheter assembly having a first circumferential rim 19a and a second circumferential rim 19b arranged on the inner surface of the catheter tube 10. The first circumferential rim 19a and the second circumferential rim 19b form compression locations to couple the expandable part 21 to the catheter tube 10. These form-fit connections have the advantage that they can provide a very reliable mechanical coupling between the expandable part 21 and the desired compression location catheter tube 10. Furthermore, the first circumferential rim 19*a* and the second circumferential rim 19*b* define the location of the expandable part with respect to the catheter tube. This enables the user to place the expandable part 21 precisely at the desired compression location, i.e. at the first circumferential rim 19*a* (as shown in FIG. 6*a*) or the second circumferential rim 19*b*. The expandable part 21 can for example, when partly expanded, be moved in proximal direction through the longitudinal channel 13, until the expandable part 21 will be stopped by respective circumferential rim 19*a*, 19*b*, indicating that the desired compression location is reached.

FIGS. 7*a*, 7*b*, 7*c* and 7*d* show, as an example, different states in which the guide wire-catheter assembly 1 may be used.

Figures 7A, 7B, 7C, 7D:
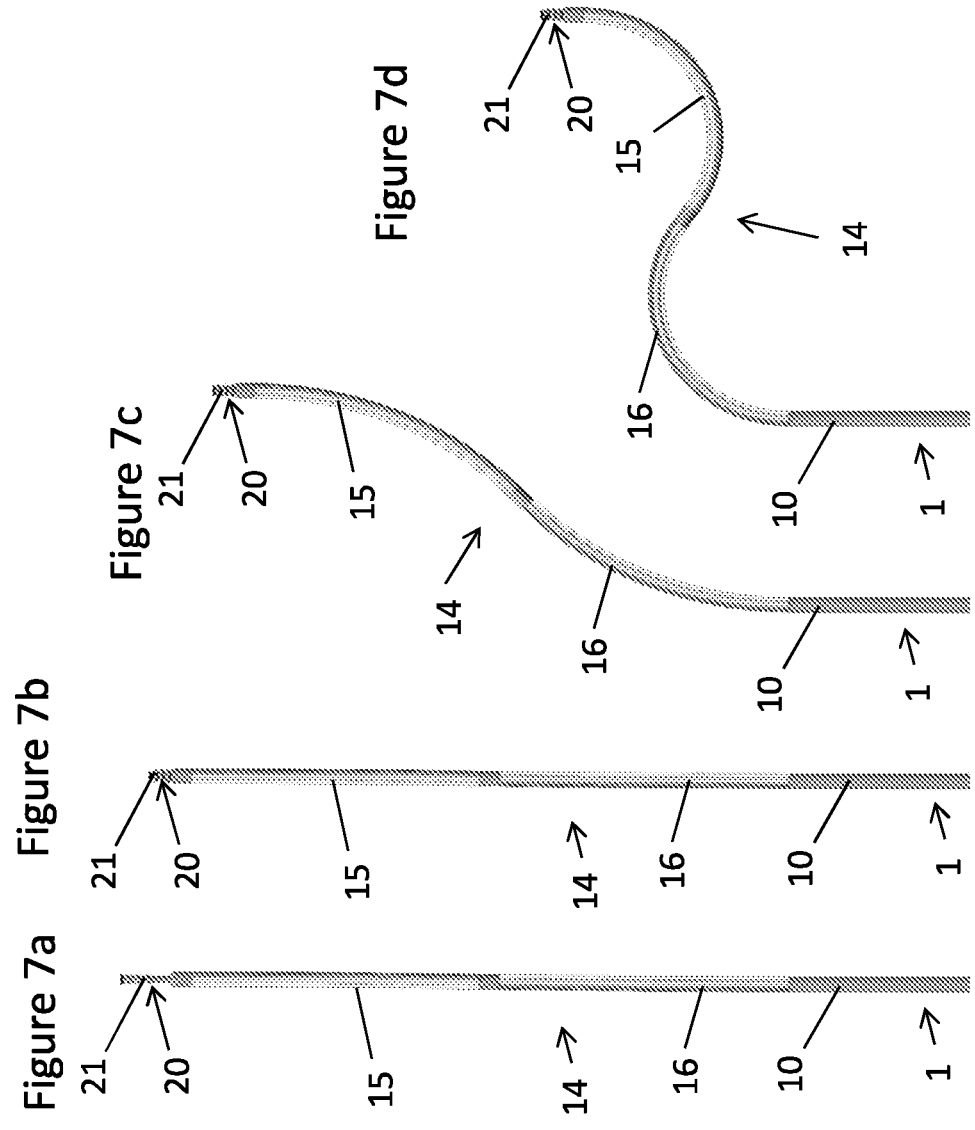
FIGS. 7a, 7b, 7c and 7d show the guide wire-catheter assembly of FIG. 1 in different bending states.

FIG. 7*a* shows the guide wire-catheter assembly 1 in a first state, corresponding to the state as shown in FIG. 1. The expandable tip part 21 extends distal from the catheter tube 10, and is in the non-expanded state. The catheter tube 10 and the guide wire 20 can be moved together through a human or animal body lumen, but also independent from each other in longitudinal direction. The guide wire can be pulled, in proximal direction, completely out of the catheter tube 10, but also the catheter tube 10 can be pulled completely in the proximal direction, while the guide wire 20 remains in a human or animal body lumen. The bendable part 14 is in a free state, in which no longitudinal compression force is exerted thereon by the guide wire 20.

FIG. 7*b* shows a second state of the guide wire-catheter assembly 1, in which the expandable tip part 21 has been moved into the expanded position by relative movement of the guide wire core 22 with respect to the guide wire sleeve 23. The expanded tip part 21 has been moved against the distal end surface 17, but is not pulled against the distal end surface 17 with a substantial force. As a result, the bendable part 14 is still relatively straight since no longitudinal compression force is exerted on the bendable part 14.

FIG. 7*c* shows a third state of the guide-wire catheter assembly 1, in which a substantial force is exerted by the expandable tip part 21 on the distal end surface 17 of the catheter tube 10. Due to this longitudinal compression force in the bendable part 14, the bendable part 14 is bent into an S-shape, as a result of the distribution of the first and second material parts 15*a*, 15*b* over the circumference of the distal bendable part 15 and the distribution of the first and second material parts 16*a*, 16*b* over the circumference of the proximal bendable part 16.

FIG. 7*d* shows a fourth state of the guide wire-catheter assembly 1 in which, compared with the third state, the longitudinal compression force exerted by the expandable tip part 21 on the distal end surface 17 is further increased. This results in that the degree of bending of the bendable part 14 is further increased.

It will be clear to the skilled person that the specific S-shape of the bendable part 14 results from the distribution, stiffness and lengths of the several material parts 15*a*, 15*b*, 16*a*, 16*b* of the bendable sub-parts 15, 16. Variations in the length, stiffness, distribution etc. may result in a different bending shape. For example, also only one, or three or more bendable sub-parts may be provided in the bendable part 14. The desired bending shapes may be determined and selected in dependence of the application in which the guide wire-catheter assembly 1 is used, in particular along which pathway the guide wire-catheter assembly 1 should be advanced through a luminal system.

Further, it is remarked that, in the above embodiment, the expandable tip part 21 is used to exert a longitudinal compression force on a distal end surface 17 of the catheter tube 10. It may be contemplated that also other locations may be selected to exert a longitudinal compression force on a bendable part of a catheter tube 10. Typically, these locations are arranged distally of (at least a part of) the bendable part 14. For example, in the embodiment shown in FIG. 1, a second location for exerting a longitudinal compression force may be provided between the distal bendable sub-part 15 and the proximal bendable sub-part 16. In such case, the longitudinal compression force will only actively bend the proximal bendable sub-part 16, while no bending is created in the distal bendable sub-part 15.

Figure 8:
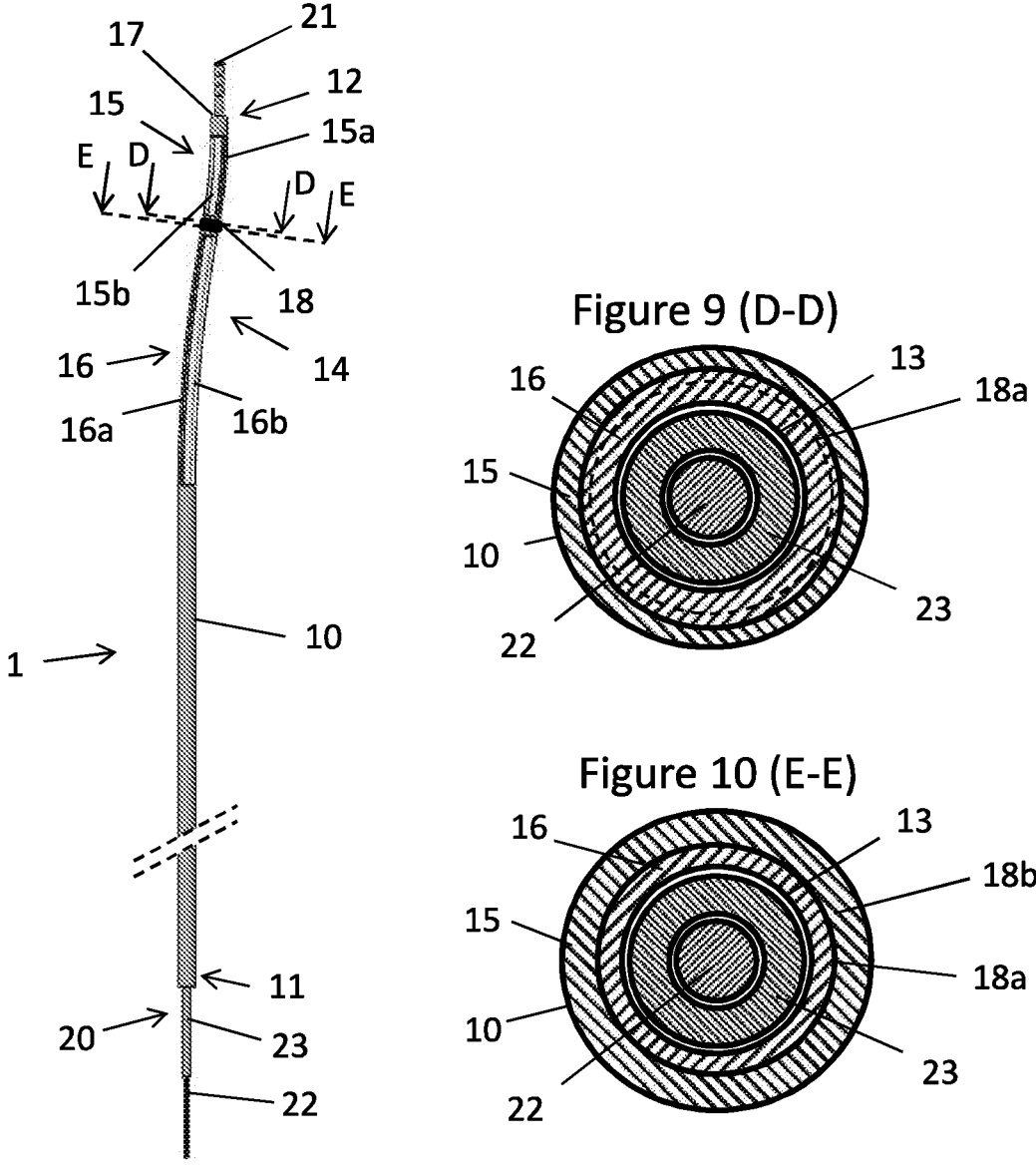
FIG. 8 shows a guide wire-catheter assembly according to an alternative embodiment of the invention.

FIG. 8 shows an alternative embodiment of a guide wire-catheter assembly 1. The same parts, or parts having substantially the same function, will be designated by the same reference numerals.

A main difference between the guide wire-catheter assembly 1 of FIG. 1 and the guide wire-catheter assembly 1 of FIG. 8 is the construction of the distal bendable sub-part 15.

In the embodiment of FIG. 1, the length of the distal bendable sub-part 15 and the proximal bendable sub-part 16 is substantially the same. In the embodiment of FIG. 8, the length of the distal bendable sub-part 15 is substantially smaller that the length of the proximal bendable sub-part 16.

Further, in the embodiment of FIG. 8, a rotation coupling 18 is provided between the distal bendable sub-part 15 and the proximal bendable sub-part 16. This rotation coupling 18 allows the distal bendable sub-part 15 to be rotated about the longitudinal axis of the catheter tube 10 with respect to the proximal bendable sub-part 16, in order to adjust the bending direction of the distal bendable sub-part 15 with respect to the bending direction of the proximal bendable sub-part 16

FIGS. 9 and 10 show cross sections D-D and E-E of the rotation coupling 18. The rotation coupling 18 comprises a circumferential groove 18*a* provided in the proximal bendable sub-part 16 and a circumferential inner rim 18*b* provided on the distal bendable sub-part 15. The inner rim 18*b* is configured to extend into the groove 18*a* in order to obtain a rotatable connection between the distal bendable sub-part 15 and the proximal bendable sub-part 16.

FIG. 9 shows a cross section above the groove 18*a*, in which the groove 18*a* is indicated by a dashed line. It can be seen that the outer diameter of the proximal bendable sub-part 16 is larger than the diameter of the bottom of the groove 18*a*. The inner diameter of the distal bendable sub-part 15 substantially corresponds with the outer diameter of the proximal bendable sub-part 16.

FIG. 10 shows a cross section of the rotation coupling at the location of the groove 18*a*. It can be seen that, due to the groove 18*a*, the outer diameter of the proximal bendable sub-part 16 is smaller with respect to the cross section of FIG. 9, and, due to the inner rim 18*b*, the inner diameter of the distal bendable sub-part 15 is correspondingly smaller.

The rotation coupling 18 allows rotation of the distal bendable sub-part 15 with respect to the proximal bendable sub-part 16 in order to adjust the shape of the bendable part 14, but the rotation coupling 18 prevents that the distal bendable sub-part 15 can be separated from the proximal bendable sub-part 16, when a pulling force is exerted on the distal bendable sub-part 15 in a distal direction. However, it may be possible that the distal bendable sub-part 15 can be separated from the proximal bendable sub-part 16, when an excessive pulling force is exerted in distal direction on the distal bendable sub-part 15.

In the embodiment of FIG. 8, the rotational position of the distal bendable sub-part 15 can only be adjusted by direct manipulation of the distal bendable sub-part 15. In order to adjust a rotational position of the distal bendable sub-part 15, the catheter tube 10 may be pulled out of a human or animal body lumen to make this direct manipulation possible.

To prevent inadvertent rotation of the distal bendable sub-part 15 with respect to the proximal bendable sub-part 16, the rotation coupling 18 may provide some friction between these parts.

FIG. 11 shows a further alternative embodiment of a guide wire-catheter assembly 1. In this embodiment, the catheter tube 10 comprises a catheter outer tube 10a and a catheter inner tube 10b. FIG. 12 shows a cross section F-F of the guide wire-catheter assembly 1 of FIG. 11 showing the catheter outer tube 10a and the catheter inner tube 10b.

The catheter outer tube 10a comprises the proximal bendable sub-part 16, while the catheter inner tube 10b is connected to the distal bendable sub-part 15. At the proximal end 11 of the catheter tube 10, the catheter inner tube 10b protrudes in proximal direction from the catheter outer tube 10a. This protruding part of the catheter inner tube 10b enables the user, by rotation of the catheter inner tube 10b with respect to the catheter outer tube 10a, to rotate the distal bendable sub-part 15 with respect to the proximal bendable sub-part 16, while a substantial length of the guide wire-catheter assembly 1 is arranged within a human or animal body lumen.

Figures 13, 14:
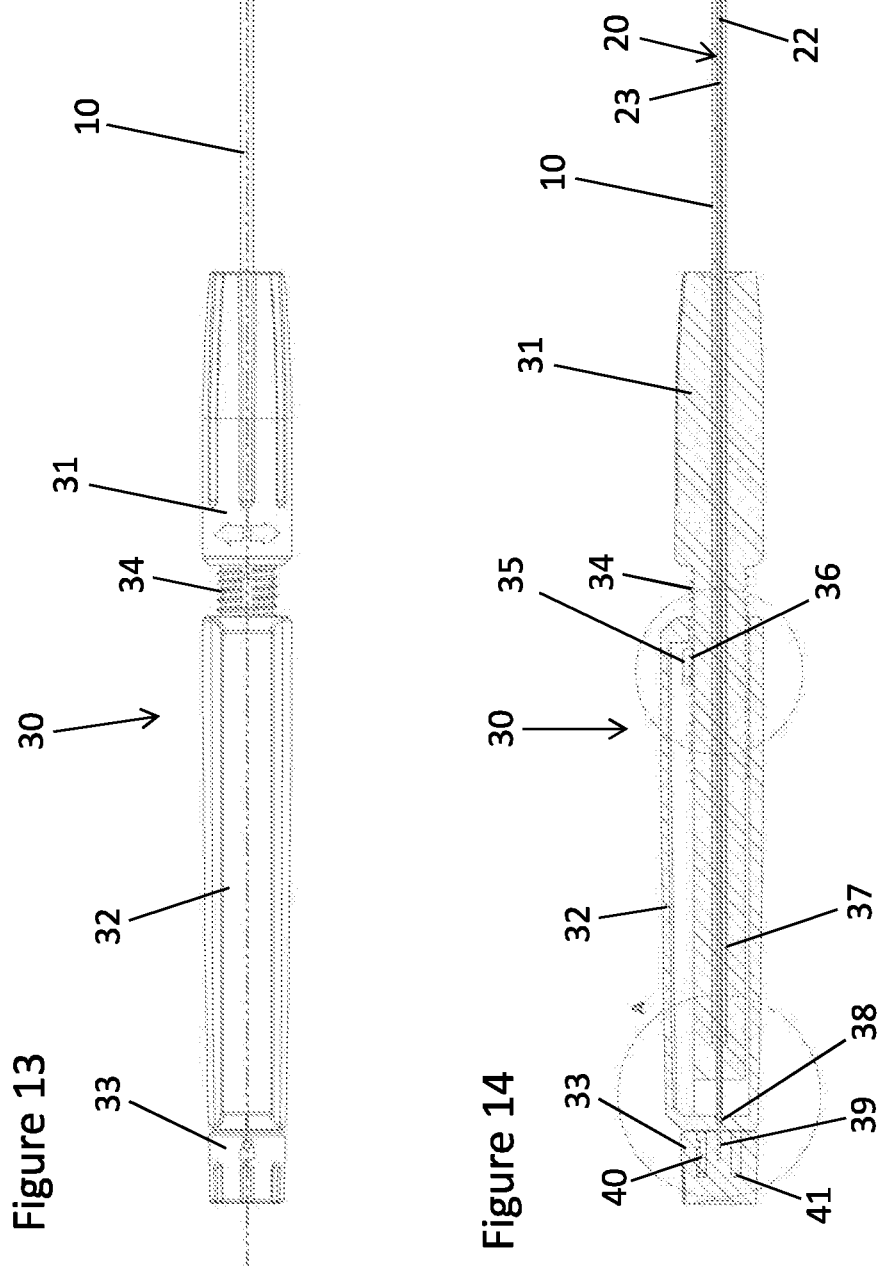
FIG. 13 shows a top view of an embodiment of an operating device of the guide wire-catheter assembly
FIG. 14 shows a cross-section of the operating device of FIG. 13.

FIG. 13 shows a top view of an operating device 30 to operate the guide-wire catheter assembly 1. FIG. 14 shows a longitudinal cross section of the operating device 30.

The operating device 30 is arranged to control the relative position of a proximal end of the guide wire 20 with respect to a proximal end of the catheter tube 10 and to lock the relative position of the guide wire core 22 with respect to the guide wire sleeve 23. It is remarked that FIGS. 13 and 14 only partly show the catheter tube 10, the guide wire core 22 and the guide wire sleeve 23. The operating device 30 comprises a first operating part 31, a second operating part 32 and a guide wire lock knob 33.

The first operating part 31 comprises an outer screw thread 34 arranged on an outer surface of the first operating part 31. The second operating part 32 comprises an inner screw element 35 having an inner screw thread 36 that cooperates with the outer screw thread 34.

The proximal end of the catheter tube 10 is fixed to the first operating part 31, for example clamped or glued in a fixation channel 37 of the first operating part 31. The proximal end of the guide wire sleeve 23 is fixed to the second operating part 32 at a first fixation location 38. The proximal end of the guide wire core 22 is fixed to the guide wire lock knob 33 at a second fixation location 39.

The guide wire lock knob 33 can be arranged in two locking positions.

Figure 15:
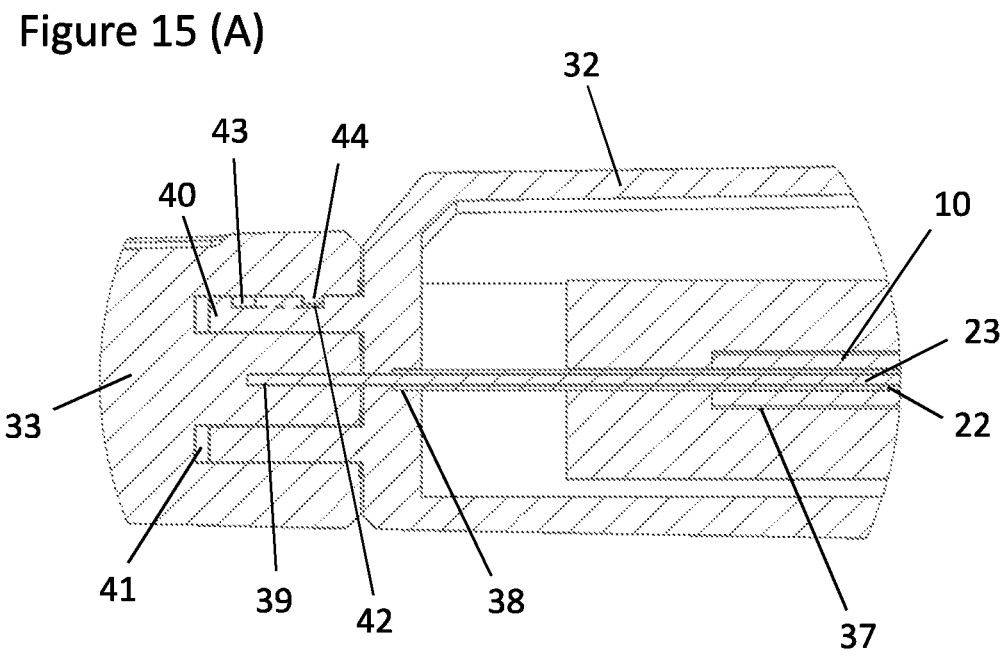
FIG. 15 shows a detail of FIG. 13 with the guide wire lock knob in a first locking position.
Figure 16:
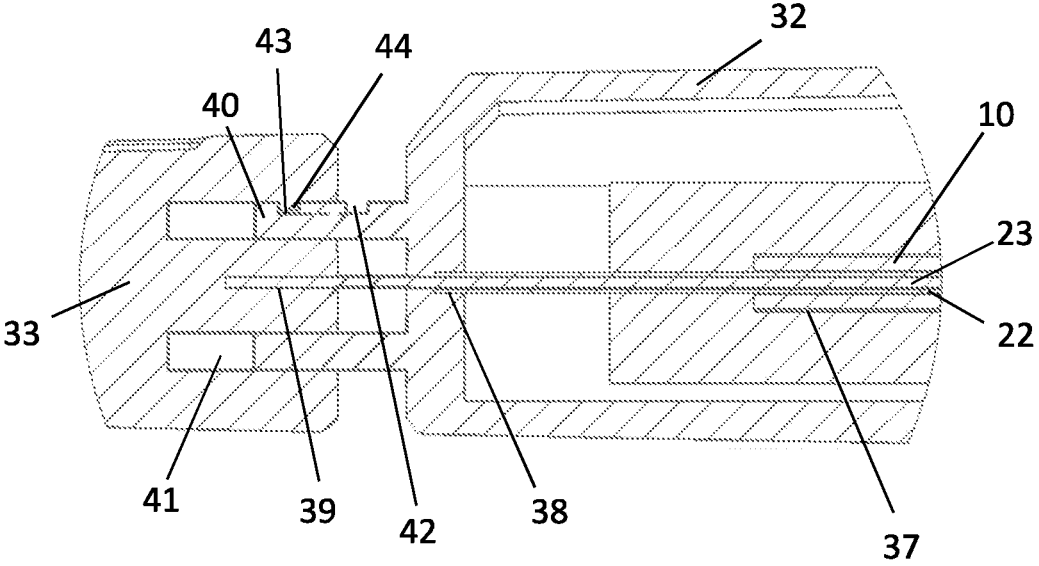
FIG. 16 shows a detail of FIG. 13 with the guide wire lock knob in a second locking position.

FIG. 15 shows the guide wire lock knob 33 in a first locking position. FIG. 16 shows the guide wire lock knob 33 in a second locking position.

The second operating part 32 comprises an annular extension 40 that is arranged in a corresponding annular recess 41 of the guide wire lock knob 33. The annular extension 40 comprises a first slot 42 extending in tangential direction over a part of the circumference of the annular extension 40 and a second slot 43 also extending in tangential direction over a part of the circumference of the annular extension 40.

The guide wire lock knob 33 comprises a protrusion 44 that, in the first locking position, is arranged in the first slot 42, and, in the second locking position, is arranged in the second slot 43. The first slot 42 and the second slot 43 are connected with each other with a longitudinal groove (indicated by a dashed line). This longitudinal groove is arranged at an angular distance with respect to the location of the protrusion 44 shown in FIG. 15.

In the first locking position, as shown in FIG. 16, the guide wire lock knob 33 is arranged against the second operating part 32, such that the first fixation location 38 and the second fixation location 39 are arranged relatively close to each other. This position corresponds to a relative position of the guide wire core 22 with respect to the guide wire sleeve 23, in which the guide wire core 22 is moved relatively far into the guide wire sleeve 23. In this relative position of the guide wire core 22 with respect to the guide wire sleeve 23, the expandable part 21 is arranged in the non-expanded position. In this position the guide wire 20 can be moved through the longitudinal channel 13 of the catheter tube 10 without a compression force being exerted on the catheter tube 10. This first locking position may for example be used when the guide wire needs to be pulled out of the catheter tube 10 or when the expandable part 21 has to be moved to another compression location.

In the second locking position, as shown in FIG. 16, the guide wire lock knob 33 is further away from the second operating part 32. The guide wire lock knob 33 can be moved from the first locking position to this second locking position by rotation of the guide wire lock knob 33 such that the protrusion 44 is rotated through the first slot 42 until it is located in the longitudinal groove. In the longitudinal groove the guide wire lock knob 33 can be moved away from the first operating part 32.

This movement will pull the guide wire core 22 in proximal direction with respect to the guide wire sleeve 23. Due to this movement of the guide wire core 22 in proximal direction, the expandable part 21 will be placed in the expanded position. By rotation of the protrusion 44 into the second slot 43, the guide wire lock knob 33 can be locked in the second locking position, as shown in FIG. 16. The expandable part 21 is now arranged in the expanded position. In this expanded position, the expandable part 21 can be used to exert a compression force at a compression location, for example on the distal end surface 17 of the catheter tube 20.

By rotation of the first operating part 31 with respect to the second operating part 32, the distance between the fixation channel 37 and the first fixation location 38 may be adjusted. Such adjustment results in a longitudinal displacement of the proximal end of the guide wire 20 with respect to the proximal end of the catheter tube 10. When the expandable part is arranged, in expanded position, at a compression location, the longitudinal displacement of the proximal ends of the guide wire 20 and the proximal end of the catheter tube 10 with respect to each other can be used to adjust the degree of bending of the bendable part 14. The screw thread connection between the first operating part 31 and the second operating part 32 therefore can also be used to maintain the catheter tube 10 in a fixed relative position with respect to the guide wire 20, to therewith maintain the degree of bending of the bendable part 14.

When the expandable part 21 is in the non-expanded position, the rotation of the first operating part 31 with respect to the second operating part 32, may also be used to displace the expandable part 21 with respect to the catheter tube 10, for example to move the expandable part 21 to another compression location. Also, when the expandable part 21 extends distally out of the longitudinal channel 13 of the catheter tube 10, the expandable part 21, in expanded position, can be moved towards and against the distal end surface 17 by rotation of the first operating part 31 with respect to the second operating part 32

The operating device 30 is designed such that the second operating part 32 of the operating device 30 can be held in a single hand, while one or more fingers are used to rotate the first operating part 31 with respect to the second operating part 32 to adjust the degree of bending of the catheter tube 10. The guide wire lock knob 30 will typically be operated by a second hand of the user.

The inner screw element 35 is movable between a mating position, as shown in FIG. 14, in which the inner screw thread 36 mates with the outer screw thread 34 of the first operating position and a free position in which the inner screw thread 36 does not mate with the outer screw thread 34. In particular, in the free position, the inner screw element 35 is spaced in radial direction from the outer screw thread 34, so that the outer screw thread 34 and the inner screw thread 36 no longer engage each other.

In this free position, the first operating part 31 can freely slide in longitudinal direction with respect to the second operating part 32 without the need of making a rotational screw movement between the first operating part 31 and the second operating part 32. This allows for example a relative easy and quick movement to displace the guide wire 20 with respect to the catheter tube 10.

This sliding movement is for example useful to pull the guide wire 20 out of the catheter tube 10 or to move the expandable part quickly to another compression location. During this movement, the guide wire lock knob 33 should be arranged in the first locking position (FIG. 15) such that the expandable part 21 is in the non-expanded position and does not hinder relative movement of the guide wire 20 with respect to the catheter tube 10.

The inner screw element 35 may be biased by a spring in the mating position. A separate actuator, for example button, may be provided to move the inner screw element 35 to the free position.

Figure 17:
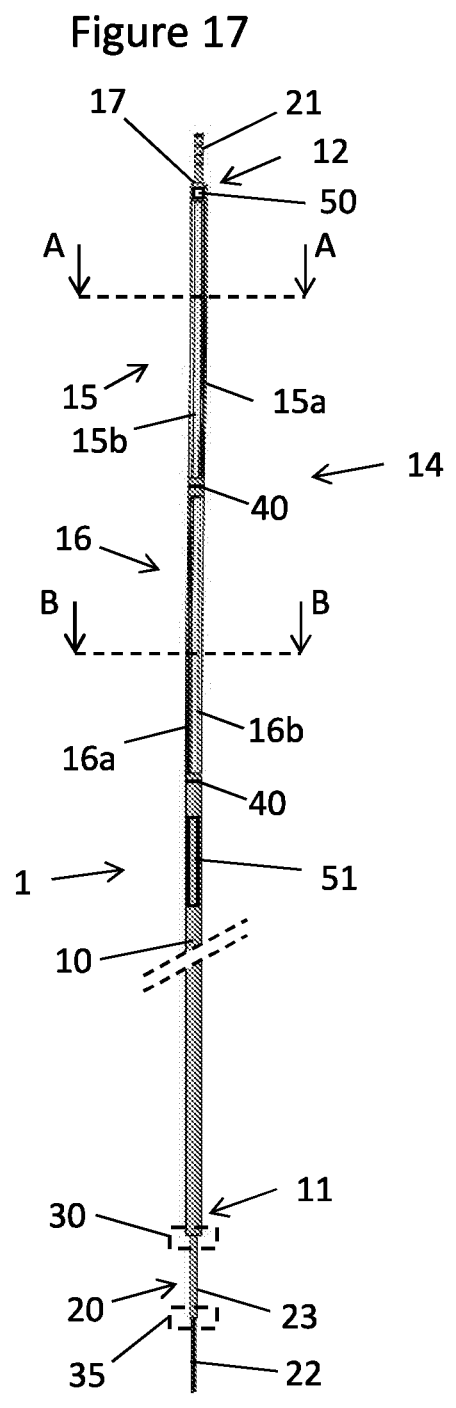

FIG. 17 discloses a guide wire-catheter assembly 1 generally having the same construction as the guide wire-catheter assembly 1 of FIG. 1. Same parts or parts having substantially the same function are indicated by the same reference numerals. The catheter tube 10 of FIG. 17 comprises a pH sensor 50 at the distal end of the catheter tube 10, and at least one bending sensor 51 arranged on or in the catheter tube 10.

The pH sensor 50 can be used to obtain a pH sensor signal representative for the pH value at the location where the pH sensor is positioned. The bending sensor 51 is configured to provide a sensor signal representative for a degree of bending of the catheter tube at the location of the bending sensor 51. The bending sensor may for example be an electric sensor such as a piezoelectric sensor or wire strain gauge, or an optical sensor.

The bending sensor 51 and the pH sensor 50 can be used to determine whether the catheter tube 10, in particular a feeding tube, is properly positioned in a patient.

A feeding tube is a catheter tube to be placed through a mouth or a nose of a patient into the stomach or small intestine of the patient. Such feeding tube may for instance be nasogastric feeding tube, a nasojejunal feeding tube, a nasoduodenalm feeding tube, an orogastric feeding tube, an orojejunal feeding tube, or an oroduodenal feeding tube.

It may be a challenging task to place a feeding tube into a patient usually requiring placement and removal of an endoscope. This procedure is inconvenient and often painful for the patient. It is therefore desirable that the catheter tube can be easily maneuvered into the patient. Further, it should be avoided that the catheter tube is improperly placed in the patient which would require removal and renewed placement of the catheter tube.

It has been found that the guide wire-catheter assembly 1 can advantageously be used for the placement of a feeding tube into a desired position in the gastrointestinal tract. Bending of the bendable part 14 of the catheter tube 10, by pulling the guide wire in proximal direction while the expandable part 21 is in the expanded position, can be used to facilitate advancing of the catheter tube along the desired insertion path to a desired position. The bending of the bendable part 14 can be carried out as described hereinabove with respect to the other embodiments.

The pH sensor 50 can be used to determine in which part of the gastrointestinal tract the catheter tube 10 is arranged. The pH value in the stomach is substantially lower than the pH value in the small intestine of a person. Therefore, an increase in pH value can be used to determine that the catheter tube has been properly advanced from the stomach into the small intestine. Correspondingly, other passages between different parts of the gastrointestinal tract that typically have distinct pH values can properly be detected.

The bending sensor 51 can be used to determine whether the actual bending of the catheter tube 10 corresponds with the expected bending of the catheter tube 10 when it extends along the intended insertion path. If the actual bending substantially deviates from the expected bending, it may be concluded that the catheter tube is not properly brought into the patient. For example, excessive bending may indicate that the catheter tube coils up in the stomach instead of running into the small intestine of the patient.

In FIG. 17, one bending sensor 51 is shown. In practice, multiple bending sensors 51 may be provided along the length of the catheter tube 10 to determine the actual bending of the catheter tube 10 at each of the measurement locations of the multiple bending sensors 51. However, one or a limited number of bending sensors 51 may also be applied, for example when only a degree of bending of a specific part of the catheter tube 10 needs to be known.

The invention claimed is:

1. A guide wire-catheter assembly, comprising:
   a catheter tube having a longitudinal channel, and
   a guide wire configured to be movable in the longitudinal channel and arranged to maneuver and guide the catheter tube through a human or animal body to locate the catheter tube at a desired location,
   wherein the catheter tube comprises a bendable part near its distal end, wherein the bendable part comprises, in a circumferential direction of the catheter tube, a varying flexibility, such that exerting a longitudinal compression force in a proximal direction at a compression location distally of the bendable part results in bending of the bendable part,
   wherein the bendable part comprises a first material extending over a first part of a circumference of the catheter tube, and a second material extending over a second part of the circumference of the catheter tube, wherein the first material has a first stiffness and the second material has a second stiffness, wherein the first stiffness is larger than the second stiffness, such that exerting a longitudinal compression force causes bending of the bendable part in a predefined bending direction, or
   wherein grooves, recesses or openings are provided to decrease stiffness on one side of the catheter tube and/or reinforcements are provided to increase stiffness on another side of the catheter tube, such that exerting a longitudinal compression force causes bending of the bendable part, and wherein the guide wire comprises an expandable part, wherein the expandable part is movable between a non-expanded position, in which a cross section of the expandable part is smaller than a smallest cross section of the longitudinal channel of the catheter tube, and an expanded position, in which a cross section of the expandable part is larger than the smallest cross section of the longitudinal channel of the catheter tube, wherein, when the expandable part is in the non-expanded position, the guide wire can be moved completely in and out of the longitudinal channel of the catheter tube, wherein, when the expandable part is in the expanded position, the expandable part is configured to exert the longitudinal compression force on the compression location in order to bend the bendable part of the catheter tube;

wherein the bendable part of the catheter tube, excluding grooves, recesses or openings, has a constant thickness in the circumferential direction, and wherein the catheter tube and the guide wire are arranged concentrically with respect to each other when the expandable part is in the expanded position such that the bendable part will bend in the predefined bending direction when a compression force is exerted on the bendable part, independent of the rotational position of the guide wire, and wherein the compression location of the catheter tube is formed by a distal end surface of the catheter tube defining a distal opening of the longitudinal channel, wherein when the expandable part exerts the longitudinal compression force on the compression location, a contact surface between the expandable part and the distal end surface of the catheter tube is ring shaped and extends around the distal opening.

2. The guide wire-catheter assembly of claim 1, wherein the expandable part is arranged at or near a distal end of the guide wire.

3. The guide wire-catheter assembly of claim 1, wherein the guide wire comprises a guide wire sleeve and a core wire, wherein the expandable part is movable between the non-expanded position and the expanded position by longitudinal movement between the guide wire sleeve and the core wire.

4. The guide wire-catheter assembly of claim 3, wherein the expandable part comprises a bellows shaped sleeve part, wherein one end of the bellows is connected to the core wire and the other end of the bellows is connected to the guide wire sleeve.

5. The guide wire-catheter assembly of claim 3, wherein the guide wire-catheter assembly comprises an operating device to lock the relative position of the core wire with respect to the guide wire sleeve in at least a first locking position in which the expandable part is arranged in the non-expanded position and a second locking position in which the expandable part is arranged in the expanded position.

6. The guide wire-catheter assembly of claim 3, wherein the guide wire-catheter assembly comprises an operating device to adjust a relative position of a proximal end of the guide wire with respect to a proximal end of the catheter tube.

7. The guide wire-catheter assembly of claim 6, wherein the operating device comprises a first operating part and a second operating part, wherein the first operating part comprises a first screw thread and the second operating part comprises a second screw thread mating with the first screw thread, wherein the proximal end of the catheter tube is fixed to the first operating part and the proximal end of the guide wire is connected to the second operating part.

8. The guide wire-catheter assembly of claim 1, wherein the bendable part comprises a first bendable sub-part and a second bendable sub-part, wherein the first bendable sub-part is configured to bend in a first bending direction, and wherein the second bendable sub-part is configured to bend a second bending direction.

9. The guide wire-catheter assembly of claim 8, wherein the first bendable sub-part and the second bendable sub-part each comprise a first material, extending over a first part of a circumference of the catheter tube, and a second material extending over a second part of the circumference of the catheter tube, wherein the first material has a first stiffness and the second material has a second stiffness, wherein the first stiffness is larger than the second stiffness, such that exerting a longitudinal compression force causes bending of the first bendable sub-part and bending of the second bendable sub-part.

10. The guide wire-catheter assembly of claim 8, wherein the first bending direction and the second bending direction are different.

11. The guide wire-catheter assembly of claim 1, wherein the bendable part comprises a first bendable sub-part and a second bendable sub-part, wherein the first bendable sub-part is configured to bend in a first bending direction, and wherein the second bendable sub-part is configured to bend in a second bending direction, and wherein the second bendable sub-part is rotatable about a longitudinal axis of the catheter tube with respect to the first bendable sub-part, to adjust the first bending direction with respect to the second bending direction.

12. The guide wire-catheter assembly of claim 11, wherein the first bendable sub-part and the second bendable sub-part are connected to each other by a rotation coupling, that allows rotation of the first bendable sub-part and the second bendable sub-part with respect to each other.

13. The guide wire-catheter assembly of claim 11, wherein the first bendable sub-part is arranged distally from the second bendable sub-part, wherein the catheter tube comprises a catheter outer tube and a catheter inner tube, wherein the catheter inner tube is at least partially arranged in the catheter outer tube, and wherein the first bendable sub-part is connected to the catheter inner tube and wherein the second bendable sub-part is connected to the catheter outer tube.

14. The guide wire-catheter assembly of claim 1, wherein an outer diameter of the catheter tube is maximally 3.0 mm.

15. The guide wire-catheter assembly of claim 14, wherein an outer diameter of the catheter tube is maximally 2.5 mm.

16. The guide wire-catheter assembly of claim 14, wherein an outer diameter of the catheter tube is maximally 2.0 mm.

17. The guide wire-catheter assembly of claim 1, wherein an outer diameter of the guide wire with the expandable part in non-expanded position is maximally 1.0 mm.

18. The guide wire-catheter assembly of claim 17, wherein an outer diameter of the guide wire with the expandable part in non-expanded position is maximally 0.8 mm.

19. The guide wire-catheter assembly of claim 1, wherein the guide wire-catheter assembly comprises one or more markers of radiopaque material.

20. The guide wire-catheter assembly of claim 1, wherein the catheter tube comprises multiple compression locations.

21. The guide wire-catheter assembly of claim 1, wherein the catheter tube comprises a sensor configured to provide a sensor signal representative for a degree of bending of the catheter tube.

22. The guide wire-catheter assembly of claim 1, wherein the catheter tube is a feeding tube to be placed through a mouth or a nose of a patient into the stomach or small intestine of the patient.

23. The guide wire-catheter assembly of claim 1, wherein the catheter tube comprises a pH sensor configured to provide a pH sensor signal representative for a pH value at a location of the pH sensor.

24. The guide wire-catheter assembly of claim 1, wherein the guide wire-catheter assembly comprises a locking device to lock a position of the guide wire with respect to the catheter tube.

\* \* \* \* \*